United States Patent
Boda

(10) Patent No.: US 7,981,033 B2
(45) Date of Patent: Jul. 19, 2011

(54) DIAGNOSTIC PROBE AND KIT FOR TONOMETRIC EXAMINATION OF RESPIRATORY INSUFFICIENCY AND REGIONAL PERFUSION FAILURE OF THE BODY

(75) Inventor: Domokos Boda, Szeged (HU)

(73) Assignee: Szegedi Tudomanyegyetem, Szeged (HU), part interest ( * ) Notice: Subject to any disclaimer, the term of this patent is extended or adjusted under 35 U.S.C. 154(b) by 339 days.

(21) Appl. No.: 10/576,517

(22) PCT Filed: Nov. 4, 2004

(86) PCT No.: PCT/HU2004/000103
§ 371 (c)(1), (2), (4) Date: May 7, 2007

(87) PCT Pub. No.: WO2005/041764
PCT Pub. Date: May 12, 2005

(65) Prior Publication Data
US 2008/0058666 A1 Mar. 6, 2008

(30) Foreign Application Priority Data
Nov. 4, 2003 (HU) ................................. 0303605

(51) Int. Cl.
*A61B 5/00* (2006.01)
(52) U.S. Cl. .................. 600/363; 600/300; 600/529

(58) Field of Classification Search .................. 600/364, 600/529, 300
See application file for complete search history.

(56) References Cited

U.S. PATENT DOCUMENTS

| | | | | |
|---|---|---|---|---|
| 5,408,999 A | * | 4/1995 | Singh et al. | 600/342 |
| 5,423,320 A | | 6/1995 | Salzman et al. | |
| 5,957,839 A | * | 9/1999 | Kruse et al. | 600/309 |
| 6,216,024 B1 | * | 4/2001 | Weil et al. | 600/353 |
| 6,238,339 B1 | * | 5/2001 | Fiddian-Greene et al. | 600/309 |
| 6,370,941 B2 | * | 4/2002 | Nakamura et al. | 73/31.05 |
| 6,432,051 B1 | * | 8/2002 | Rantala | 600/364 |

FOREIGN PATENT DOCUMENTS
EP 0 941 693 9/1999
* cited by examiner

*Primary Examiner* — Charles A Marmor, II
*Assistant Examiner* — Karen E Toth
(74) *Attorney, Agent, or Firm* — Young & Thompson

(57) ABSTRACT

The invention relates to a tonometric device (20) for examination of respiratory insufficiency and regional tissue perfusion failure in patients, comprising a distal end (22), a section (24) to be introduced into the body, and a fixing part (3). The section (24) to be introduced comprises a first tube (1) to which an additional tubing (4) is connected. A second tube (2) is arranged substantially parallel with the first tube (1). At least the section (24) of the first tube (1) is made of a material permeable for gases, especially for carbon' dioxide, but substantially impermeable for body fluids, preferably of silicone rubber. The device does not comprise any balloon, it can be introduced into the patient stomach without preliminary preparation, and is useful for examination of premature babies.

5 Claims, 2 Drawing Sheets

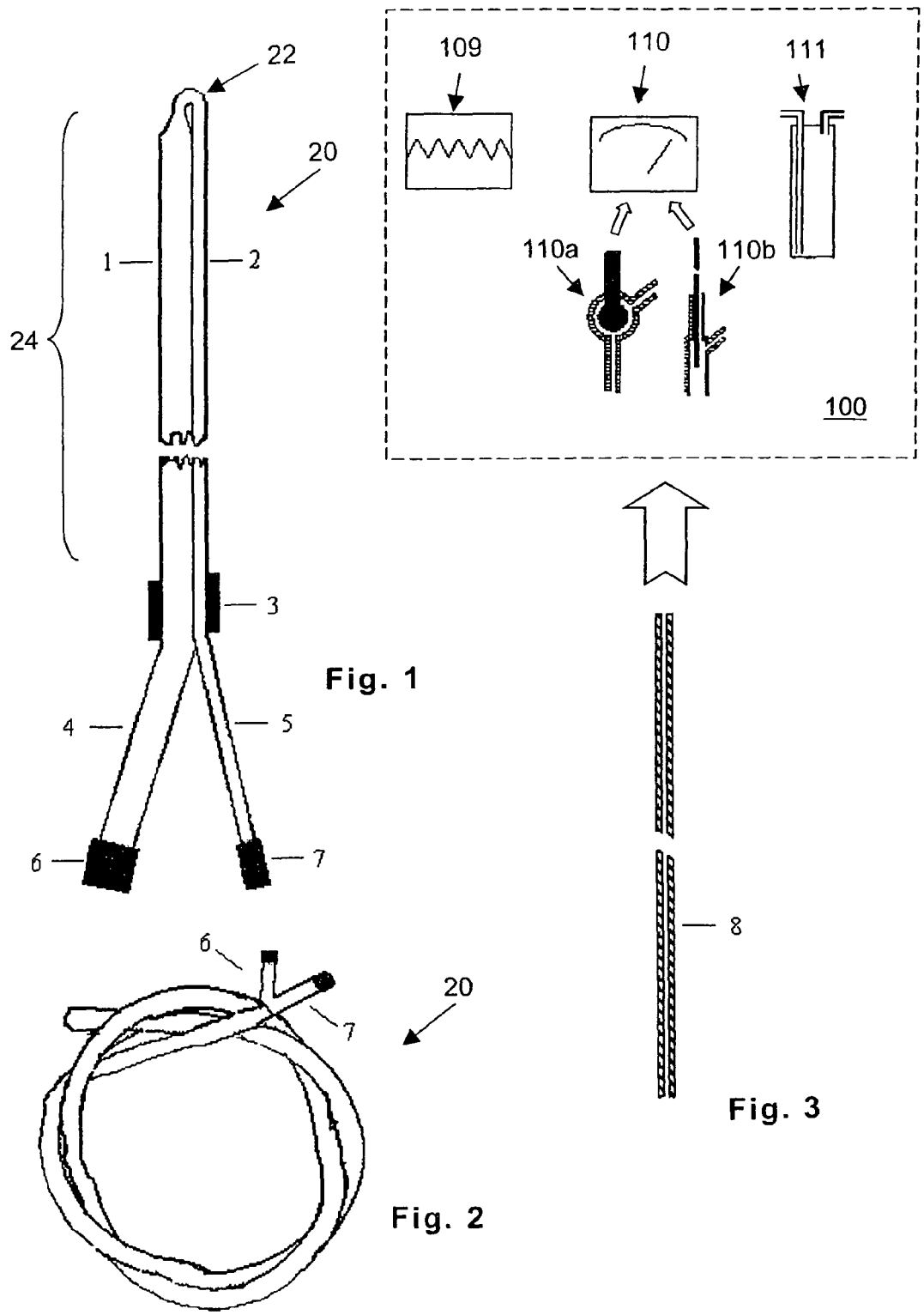

DIAGNOSTIC PROBE AND KIT FOR TONOMETRIC EXAMINATION OF RESPIRATORY INSUFFICIENCY AND REGIONAL PERFUSION FAILURE OF THE BODY

The present invention relates to a diagnostic probe and kit for tonometric examination of respiratory insufficiency and regional perfusion failure of the body.

The tonometric devices have been widely used in the medical practice for the examination of the tissue-specific partial pressure belonging to the carbon dioxide concentration in the whole gastrointestinal tract, especially in the stomach, the partial pressure of carbon dioxide being referred to as $pCO_2$, particularly as $p_gCO_2$ in the case of measuring inside the stomach and/or the gastrointestinal system. In steady-state circular conditions this value is almost equal to that of the arterial blood; therefore the method proved to be useful for detecting the failures of the respiratory regulatory system. On the contrary, in the case of patients having acute conditions because of various origins the tissue-specific $pCO_2$ value is higher than that in the blood. The difference between the two values is referred to as $pCO_2$ gap. By-examination of this gap the regional tissue perfusion failure can be detected, and from its size the severity of the particular disorder and the extent of the endangeredness of the patient can be concluded.

The experience acquired with numerous patients has shown that on the one hand tonometry is useful for controlling the respiratory performance by determining the systemic partial pressure related to carbon-dioxide concentration, and on the other hand this is the easiest, cheapest and most reliable method for predicting the hazard of acute disorders in patients and for monitoring the conditions of patients.

The U.S. Pat. No. 4,463,192 discloses a method for tonometric measurements. The device disclosed therein is a probe supplied with a balloon, which is readily permeable for gases but impermeable for other substances. This probe is introduced into the stomach, whereafter the balloon is filled with air or a liquid from outside. After a while the substance filled into the balloon takes up by diffusion the value of the carbon-dioxide concentration of the blood circulating in the gastric wall (mucous membrane) and this value can be determined by relatively simple laboratory methods.

The above-mentioned commonly used probe and method have several disadvantages. The introduction of hard and thick probes into the stomach causes discomfort to the patient, thus the method is essentially invasive. The loading time of the relatively high amount of filling liquid with carbon dioxide inside the balloon is too long, and thereafter the result must still be corrected for calculating the final data.

The U.S. Pat. No. 6,216,023 discloses a more preferable method wherein the balloon is loaded with air, and the obtained sample is analyzed with a gas analyzer (capnometer). New devices are applied for the automatic sampling of the air and the simple transport of the air by recirculation. Nevertheless, a probe supplied with a balloon is used for this method whereby it is also aggressive, and for obtaining reliable results the patients need to be pretreated with drugs. By including new devices the costs of the method are increased. An additional problem is that practically the method can only be performed on adults. Recently thin probes (with a diameter of about 2.2 mm) are used for examination of children, but even these probes are applied with balloons. However, due to the precise procedures necessary for the introduction of the probe and the sampling, these probes cannot be used in the daily routine in the case of premature babies of small weight.

For examination of tissue perfusion failure with tonometric methods electrochemical and fibre-optic sensors have also been used. U.S. Pat. Nos. 6,216,024, 6,143,150 and 6,055,447 disclose such solutions where the sensor itself is introduced with a probe into the stomach of the patient. Sometimes the measurement is performed with a sensor arranged sublingually or in the upper digestive tract, instead of the stomach. Although such sensors have several advantages: 2-3 minutes are enough for the examination which is easy to perform and is similar to the measuring temperature in the mouth, it is difficult to hold the sensor in the suitable position throughout the examination process, and there is a need of cooperation with the patient. An additional drawback is the need of frequent calibration of the sensor between the measurements. Thus, the sensors are disposable and the display units are expensive.

The object of the present invention is to provide a solution which allows easier examination with less stress for the patient, needs shorter times, and can be used on patients with any age, including infants and premature babies with small weight. Another object of the present invention is to provide a less embarrassing procedure in respect of other tasks associated with the clinical services. In order to render possible a wide-ranging use, the solution should be as cheap as possible, but at the same time it should be fast and give precise results. A further important aspect is that for determining the partial pressure of carbon dioxide in the sample or the partial pressure belonging to the concentration of the carbon dioxide dissolved in the sample, laboratory means should be usable which are -generally available in the hospitals, and the employed examination system should be choosable from various solutions depending on the prevailing conditions.

We have discovered that the drawbacks of prior art solutions can be eliminated or at least reduced by a tonometric device, which is constructed substantially as a tube without a balloon, wherein the material of at least that section of the tube which is introduced into the gastrointestinal tract is permeable for gases, especially for carbon dioxide, but impermeable for other substances of body fluids. We have also discovered that the construction of the probe forming the tonometric device is especially advantageous if the probe, comprises two parallel tubes fixed to each other and the distal ends of these tubes to be introduced into the body cavity are communicating with each other.

Based on the above, the present invention provides a novel device which allows faster, easier and cheaper $p_gCO_2$ examination which is free of invasive effects. The examination can be performed on patients of any age and is usable for fast checking even in emergency situations.

The tonometric device of the present invention for examination of respiratory insufficiency and regional tissue perfusion failure in patients comprises a distal end for introducing into the gastrointestinal tract of the body of the patient, a section to be introduced into the body, and a section fixing the position of the device to the patient, wherein the section to be introduced comprises a first tube to which an additional tubing is connected. The device further comprises a second tube arranged substantially parallel with and fixed to the first tube, wherein the distal end of the second tube is in communicating connection with the first tube, and at least the section to be introduced of the first tube is made of a material permeable for gases, especially for carbon dioxide, but substantially impermeable for body fluids and other substances, preferably of silicone rubber, and an additional tubing is connected to the second tube.

In a preferred embodiment of the tonometric device of the invention, the diameter of the first and second tubes is substantially constant between the distal end and the fixing section of the tubes.

In another preferred embodiment of the tonometric device of the invention, the additional tubings are provided with connecting means.

In an another preferred embodiment of the tonometric device of the invention, the connecting means are constructed for connecting them to the connecting stub of a medical syringe.

In a further preferred embodiment of the tonometric device of the invention, the outer diameter of the tubes is from 1 to 4 mm and the wall thickness ranges from 0.3 to 1.0 mm.

In a further preferred embodiment of the tonometric device of the invention, the outer diameter of the first tube ranges from 2 to 4 mm and its wall thickness from 0.5 to 1.0 mm, and the outer diamater of the second tube ranges from 1.0 to 1.5 mm and its wall thickness from 0.3 to 0.5 mm.

In a further preferred embodiment of the tonometric device of the invention, the second tube is built together with the first tube, or the second tube is formed as a second passage in the wall surrounding the passage of the first tube.

In a further preferred embodiment of the tonometric device of the invention, the additional tubings are connected to each other and form a closed system with the tubes, wherein the closed system is filled up with an indicator-containing liquid suitable for detecting carbon-dioxide concentration.

The invention will be better understood from the following description when read in conjunction with the accompanying drawings. :

BRIEF DESCRIPTION OF THE DRAWINGS

FIG. 1 is a side view of the tonometric device of the invention.

FIG. 2 illustrates the tonometric device of FIG. 1 folded to crown shape.

FIG. 3 is a scheme of measuring possibilities performable by the tonometric device of the invention

Figure 4:
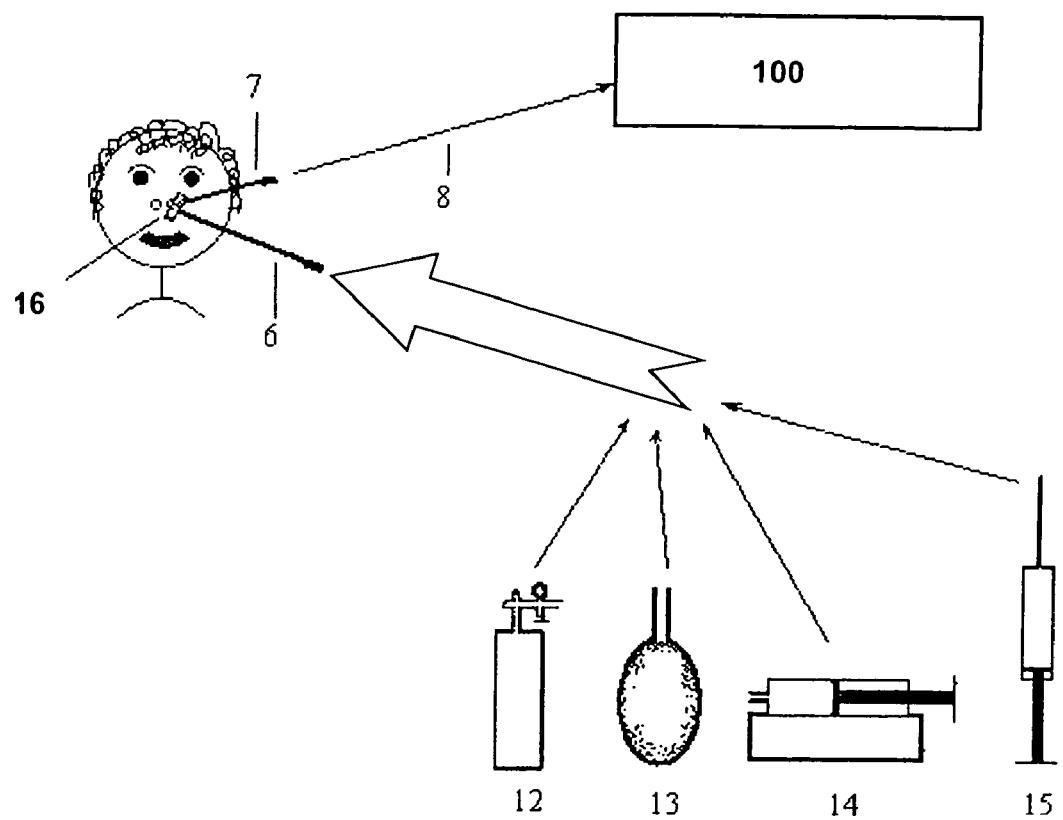
FIG. 4 is a scheme illustrating the possibilities of filling the measuring medium into or discharging it from the tonometric device of the invention.

The diameter of the tubes 1 and 2 of probe 20 can be the same or different. The probe 20 of FIG. 1 consists of a thicker tube 1 and a thinner tube 2. At the distal end of the probe 20, that is at the end of the section 24 to be introduced into the gastrointestinal tract of the patient, the tube 2 is connected to the end of the tube 1 for example with an airproof bond. This provides the continuous transferring of the test material, such as air or liquid, of the probe 20 from the one of tube 1 or 2 into the other.

The tubes 1 and 2 are joined together e.g. by sticking, starting from the distal end 22 of the part 24 of probe 20, and the two tubes are running parallel until the fixing part 3 wherein the two tubes 1 and 2 are fixed by a ring, which also serves for fixing the device to the patient. Next to the fixing part 3 the two tubes 1 and 2 split to additional tubings 4 and 5. The additional tubings 4 and 5 are ending in connecting means 6 and 7, resp., for connecting with the joint of a medical syringe and, resp., with the tube 8 transferring the test material, wherein the connecting parts are formed by pressing and bonding of a thicker tubing with corresponding internal diameter to the additional tubings 4 and 5. The additional tubing 4 and the corresponding connecting means 6 forming the continuation of the thicker tube 1 serve for feeding the test material into the probe 20, whereas the additional tubing 5 forming the continuation of the thinner tube 2 and the corresponding connecting means 7 serve for discharging the test material from the probe 20.

Figure 5:
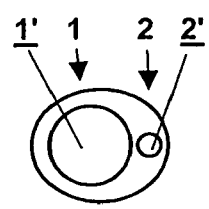
FIG. 5 is a cross-sectional view of an embodiment of the tonometric device wherein the second tube is formed inside the wall of the first tube, In a preferred embodiment the device of the present invention is a probe 20, which has a section 24 formed for introducing it into the gastrointestinal tract of the patient, and this section contains two parallel tubes 1 and 2 which are connected with each other. The material of tubes 1 and 2 should be readily permeable for gases, but substantially impermeable for any other substances, especially for other substances of the body fluids. This material can be any flexible substance, such as a plastic material, especially polymers, for example polyethylene, polyvinyl chloride, polyurethane, polyvinyl acrylate or poly-carbonate, further latex, silicone or silicone rubber.

The thinner tube 2 of the probe of the invention can be sticked for example to the opening formed in the wall of the thicker tube at the side of its distal end, wherein the one end of the thicker tube is closed. In order to provide clear connection between the first and the second tubes a monophilic fibre of suitable thickness can be placed into the thinner tube. This fibre can be pulled out later, if needed. The passage 2' of the thinner tube 2 can be formed in the surrounding wall of passage 1' of the thicker tube 1, which is illustrated in FIG. 5.

The size of the probe 20 is given by the length extending from the end 22 to the fixing section 3. An other illustrative value is the outer diameter of the thicker tube 1 of the probe 20.

The probe 20 can be made for instance with four different sizes as follows:

a) For adults the length is 65 cm, the outer diameter of the thicker tube 1 is 3 to 4 mm, preferably 4 mm; the thickness of its wall ranges from 0.5 to 1.0 mm, preferably 0.5 mm. The outer diameter of the thinner tube 2 is 1 mm, and the thickness of its wall ranges from 0.3 to 0.5 mm, preferably to 0.3 mm.

b) For children the length is 35 cm; the outer diameter of the thicker tube 1 is preferably 3 mm, and the thickness of its wall is preferably 0.5 mm. The outer diameter of the thinner tube 2 is 1 mm, and the thickness of its wall is 0.3 mm.

c) For babies the length is 27 cm, the outer diameter of the thicker tube 1 is preferably 2.5 mm, and the thickness of its wall is preferably 0.5 mm. The outer diameter of the thinner tube 2 is 1 mm, and the thickness of its wall is 0.3 mm.

d) For newborn babies the length is 20 cm, and the outer diameter of the thicker tube 1 is preferably 2 mm. The outer diameter of the thinner tube 2 is 1 mm, and the thickness of its wall is 0.3 mm.

Referring now to the FIG. 3 the alternative measurements performed by probe 20 of the tonometric device of the present invention will be described.

The steady state of $CO_2$ content between the medium as test material inside the probe 20 and the outside environment occurs along the whole length of that part of probe 20 which is inside the body cavity, that is the section 24. For displaying the results, capnometric and colorimetric measuring devices as well as measuring devices applied with a pH-measuring unit are equally suitable.

For loading probe 20 various test materials or gaseous substances such as air can be used.

If air is used as test material the ambient air also can be used. In such a case the probe 20 does not need to be loaded separately with air.

A connecting tube 8 is provided to transfer the test material from the probe 20 to the measuring unit 100. The connecting tube 8 is made of a material, which is less permeable for gases, such as polypropylene, and which has at an adequate wall thickness a low permeability for gases. For example, the connecting tube 8 has a length of 50 cm, an outer diameter of 3 mm and an inner diameter of 0.5 mm. For this purpose any polymers such as polytetrafluoro-ethylene (Teflon) or even polyvinylchloride (Tygon) can be used which have low permeability for gases. For reducing the material loss by diffusion and enhancing the accuracy of measurement the additional tubings 4 and/or 5 are also made of such material or they can be lined or covered with this material.

If the test material is air, the measuring unit 100 is preferably a capnometer, which is generally available in medical institutions and detects the partial pressure of carbon dioxide contained in the air transferred into its cell. Transferring the air as test material from the probe 20 to the capnometer is accomplished by constant flow rate in such a way that after a prescribed measuring time the test material is displaced by connecting the joint of the tube of an air-supplying device to the connecting means 6 of the thicker tube 1 of probe 20 and displacing the air being inside the probe 20 with the introduced air through the connecting tube 8 into the capnometer (FIG. 4).

Based on FIG. 4, we show now different methods for recovering the test material from the probe 20. The streaming can be performed for example with compressed air from a pressure-light pot 12 supplied with a decompressor or with a simple air-pump 13 or even with an infusion pump (14) which can be operated without any liquid. The flow rate needed for accurate measurement can be varied depending on the type of capnometer. For example this value can range from 10 to 50 ml/min for a Polaris type capnometer (JS-02260, Spegas Industries Ltd, Jerusalem). It should be noted that in the case of probes 20 for adults the transfer of the air by a medical syringe 15 also gives reliable examination results.

For children the volume of probe 20 is very small, and when the test material is transferred from the probe 20 to the capnometer, in case of too fast displacement the test material can be mixed with the introduced streaming air (or other medium), whereby the result may become unesteemable. Hence the air must be streamed slower, which prolongs the time required to transfer the test material, and thereby material loss through diffusion or leakage worsening the accuracy of the results can occur. By adoptig corresponding measures such as applying gas-proof materials, seals and connecting means as well as applying a measuring unit 100 requiring low flow rate, a person skilled in the art can get adequately reliable results with the device of the invention.

The probe 20 can be loaded with filling liquid, too. The composition of the recommended solution as a filling liquid is as follows: 150 mM common salt (NaCl), 25 mM sodium hidrogen carbonate (NaHCO$_3$), and optionally a 0.15% by w/w aqueous solution of phenolic red. The phenolic red component is required only for detecting the pH change by the discolouration of the solution. The sodium chloride and sodium hydrogen carbonate contents of the filling liquid recommended to use in the measurements are the same as in the plasma and other body fluids.

After running out of the measuring time the test material formed from the filling liquid being in equilibrium with the CO$_2$ content of the environment can be transferred to the measuring unit by a medical syringe. For this purpose the connecting stud of the syringe is placed into the connecting means 6 of the thicker tube 1 of probe 20. Then the test material is transferred for example to a pH-meter 110 by exhausting with a syringe through the connecting tube 8, or it is displaced with fresh filling liquid preloaded into the syringe, wherein the volume of the preloaded filling liquid depends on the size of the probe 20 and the type of the measuring unit; here the test material should fill up the measuring cells 110*a* or 110*b* of the pH-meter unit 110. Since the sodium hydrogen carbonate content of the test material is constant, the partial pressure of CO$_2$ in the solution can be determined from the pH value. In a state of equilibrium the relationship between the pH value of the filler liquid and the partial pressure (pCO$_2$) pertaining to the concentration of carbon dioxide are well known by a person skilled in the art, thus we do not touch upon the determination of the PCO$_2$ value. The partial pressure pertaining to the carbon dioxide concentration of the test material obtained from the probe 20 is determined with the measuring unit 100.

The pH value of the filling liquid transferred from the probe 20 into the measuring unit 110 can be determined by conventional combined pH-meter electrodes (for example in the measuring cell 110*a*). It is important to keep the CO$_2$ content of the obtained test material at a constant level; thereafter the sensor of the electrode is placed into an air-proof measuring cell 110*a* or 110*b* provided with an inlet and an outlet. In case of using a probe 20 made for adults, when the volume of probe 20 is bigger and no sparing with the test material is necessary, a measuring cell suitable to accommodate a conventional combined glass electrode can also be used. In case of using a probe 20 made for children, due to the low volume of the test material a measuring cell 110*b* of small volume can be used in which miniature (micro-) electrodes can be arranged. In such cases the electrode can be arranged in a chamber, e.g. a glass chamber, with all internal diameter of 1.5 mm and having an inlet and an outlet connection.

The determination of the pH value can be performed by examining the discolouration of the filling liquid containing phenolic red indicator. The phenolic red is a conventionally used and well proved reagent for determining the pH value of solutions. The use of it in this solution is preferred since it is not toxic, on the one hand, and the transition point of the indicator is in the pH range from 7 to 8, on the other hand, which is essential in this case. After elapsing of the prescribed measuring time, the pH value of the filling liquid, which is exhausted air-proof from probe 20, can be determined with a photometer supplied with a through-pass type measuring cell 111. When measuring with probes 20 of higher volume for adults, simple laboratory photometers are also suitable for this purpose. When measuring with low-volume probes 20 for children, photometers supplied with through-pass type capillary measuring cell are suitable. A single calibration of the different photometers is required when used for this purpose. The calibration is preferably performed with a series of buffer solutions containing 0.15% by w/w of phenolic red.

In special cases the test results can be displayed continuously. In such cases, after transferring the test material into the measuring unit 100, the pCO$_2$ value can be read on the display of the measuring unit 100 with a short delay. The fast gas diffusion occurring in the device of the invention allows further that the test material such as either air or filling liquid is streamed continuously and very slowly, e.g. at a flow rate of 4 ml/hour, to circulate it in the device forming a closed recirculating cycle. In such cases the results can be monitored continuously on the screen of the measuring unit 100, or the results can be even stored by a computer and displayed with graphic methods.

In emergency cases based on the colour change of the indicator the tissue pCO$_2$ value can be quickly estimated. In extraordinary situations when no measuring unit is available for the tonometric examination (for example in ambulance car), the p$_g$CO$_2$ value can be estimated with the test material.

exhausted from the probe 20 by comparing it with a colour scale. For this purpose the internal space of probe 20 can be as well preloaded with the test material, then the connecting means 6 and 7 can be connected with each other by the aid of a spacer, or for example with a small and preferably transparent hand-pump which is suitable for hand circulating of the test material.

In general there is no need to prepare the patient for performing the examination with probe 20 of the present invention; at most for a sensible patient an anaesthetic can be insufflated into his throat.

Based on FIG. 4 the suitable applications of the probe 20 forming the tonometric device of the invention are shown below.

By pulling out the probe 20 of corresponding size from the package wherein the probe was stored in air-proof and sterile condition or even in wet condition, for facilitating the introduction of the probe, if required a guide wire (available from Terumo Corporation, J P) is placed into the thicker tube 1 through the connecting means 6 of the additional tubing 4 until the end 22 of probe 20. A linear guide wire with a diameter of 0.5 mm for children and of a diameter of 1.0 mm for adults can be used for bracing the probe 20. Thereafter the section 24 to be introduced of the probe 20 is lubricated until the fixing section 3 by dipping into water, then it is readily introduced through the nose orifice, nose, pharynx and oesophagus until the fixing section 3 is reached. At this moment the guide wire is removed. Then the probe 20 is fixed for example with an adhesive plaster 16 next to the nose orifice to the skin of the face. After the fixation one end of the connecting tube 8 is connected to the connecting means 7 of additional tubing 5 of probe 20, whereas the other end of the connecting tube 8 is connected to the measuring unit 100. When using air as test material, there is no need to preload the probe 20. When using a measuring liquid for the examination, it is transferred into the probe 20 with a medical syringe through the connecting means 6 of the additional tubing 4 of the thicker tube 1 so that the filler liquid completely fills out the inner space of probe 20, at the same time taking care that no filler liquid be transferred to the connecting tube 8. Then we are waiting until the end of the prescribed measuring time which is approximately 15 minutes in case of using probe 20 of size a) and approximately 10 minutes in case of using probe 20 of sizes b), c) and d). During this time the test material in the probe 20 totally assumes the $pCO_2$ value of the mucous membrane of the surrounding gastrointestinal tract. After elapsing of the measuring time the test material is transferred to the measuring unit 100 as described before, and the result is read. The examination can be periodically repeated, if necessary.

The measuring of partial pressure relating to the tissue carbon-dioxide concentration can be performed in the mouth with wakeful and well co-operating patients as well as with relaxed unconscious patients (for example with anaesthetized and muscle-relaxed patients. For this purpose the above-mentioned probe 20 is likewise used. In such cases the sterile probe 20 is folded to crown shape (FIG. 2), then it is placed in the mouth of the patient until reaching the fixing section 3 and then it is fixed in the mouth cavity by an adhesive plaster. (As a matter of course, in case of examination in the mouth no guide wire for the placement of probe 20 is required). It is more safe if the probe 20 folded to crown is placed sublingually during the measuring time, but this is not absolutely necessary. However, it is important to continuously control during the measuring time that the mouth of the examined person be kept closed. Thereafter the use of the probe 20 is the same as described above in case of introducing it into the upper gastrointestinal tract.

In case of normal application the major part of the probe 20 of the invention is in the stomach; therefore the first part of the test material transferred into the measuring unit is directly derived from the sample saturated in the stomach, although the test material in the probe 20 is balanced not only with the $pCO_2$ value of the gastric mucous membrane but even with the $pCO_2$ value of the upper gastrointestinal tract. However, this circumstance does not result in any estimable error because, as it is well known for a person skilled in the art, the partial pressure of $CO_2$ in this upper tract is substantially equal to the gastric $pCO_2$ value.

As mentioned above, the invention can be used for controlling the systemic failure of the partial pressure belonging to the carbon-dioxide concentration of the body only with patients whose circulation is balanced, which must be controlled clinically. Nevertheless, the device of the invention can also be used on patients breathed through respirator since it can render unnecessary rather invasive control examinations associated with drawing blood.

A significant advantage of the present invention is the easier, faster and more tolerant detection of the tissue perfusion failure of the gastrointestinal system than in the prior art. Here we emphasize the important practical possibility that the device of the invention can be readily used with children of any age, including premature babies, without significant burden of the patients due especially to the fact that the probe 20 can be made of soft and flexible material. It is to be noted that only the outer diameter of the thicker tube should be given as thickness data of the probe 20 since the parallel adjacent thin tube increases its transversal width by approximately 1 mm only. Because of this extreme softness this causes no problem even with the youngest children. A further significant advantage is that the device of the invention can be used in emergency situations where of course only approximate results can be expected that serve only for orientation.

Although particular embodiments of the invention have been described and illustrated herein, it is recognized that modifications and variations available for those skilled in the art also fall within the scope of the invention.

The invention claimed is:

1. A tonometric device (20) for examination of respiratory insufficiency and regional tissue perfusion failure in patients comprising:
   a distal end (22) for introducing into the gastrointestinal tract of the body of a patient,
   a section (24) introduced into the body, and
   a section (3) for fixing the position of the device to the patient,
   wherein the section to be introduced (24) comprises:
   a first tube (1) to which an additional tubing (4) is connected,
   a second tube (2) arranged substantially parallel with and fixed to the first tube (1), wherein the distal end (22) of the second tube (2) is in direct communicating connection with the first tube (1) and an entire length of each of the first tube (1) and the second tube (2) are made of a material readily permeable for gases and substantially impermeable for body fluids and other substances, and an additional tubing (5) is connected to the second tube (2), wherein the outer diameter of the first tube (1) ranges from 2 to 4 mm and its wall thickness from 0.5 to 1.0 mm, and the outer diameter of the second tube (2) ranges from 1.0 to 1.5 mm and its wall thickness from 0.3 to 0.5 mm.

2. A device as claimed in claim 1, wherein the connecting means (6, 7) are constructed for connecting them to the connecting stub of a medical syringe.

3. A device as claimed in claim 1, wherein the second tube (2) is formed as a second passage (2') in the wall surrounding the passage (1') of the first tube (1).

4. The device according to claim 1, wherein the first tube (1) and the second tube (2) are made of silicone rubber.

5. The device according to claim 1, wherein a gas of the gases is carbon dioxide.

\* \* \* \* \*